(12) United States Patent
Holman et al.

(10) Patent No.: US 10,363,004 B2
(45) Date of Patent: Jul. 30, 2019

(54) METHOD OF MAKING A CUSTOMIZED INTRAORAL POSITIONING DEVICE FOR USER RADIATION THERAPY TREATMENT

(71) Applicants: RADTEC MEDICAL DEVICES, INC., San Carlos, CA (US); Ross Holman, Menlo Park, CA (US); Brian Knott, Palo Alto, CA (US)

(72) Inventors: Ross Holman, Menlo Park, CA (US); Brian Knott, Palo Alto, CA (US)

(73) Assignee: Radtec Medical Devices, Inc., San Carlos, CA (US)

( * ) Notice: Subject to any disclaimer, the term of this patent is extended or adjusted under 35 U.S.C. 154(b) by 0 days.

(21) Appl. No.: 15/966,415

(22) Filed: Apr. 30, 2018

(65) Prior Publication Data

US 2018/0242931 A1 Aug. 30, 2018

Related U.S. Application Data

(63) Continuation of application No. PCT/US2017/052821, filed on Sep. 21, 2017.
(Continued)

(51) Int. Cl.
| | |
|---|---|
| *A61B 6/14* | (2006.01) |
| *A61F 5/56* | (2006.01) |
| *A61N 5/10* | (2006.01) |
| *A61B 13/00* | (2006.01) |
| *A61B 90/00* | (2016.01) |

(Continued)

(52) U.S. Cl.
CPC ............. *A61B 6/145* (2013.01); *A61B 90/04* (2016.02); *A61N 5/1039* (2013.01); *A61B 13/00* (2013.01); *A61B 90/14* (2016.02); *A61B 90/16* (2016.02); *A61B 2090/101* (2016.02); *A61F 5/566* (2013.01); *A61N 5/1075* (2013.01);
(Continued)

(58) Field of Classification Search
CPC .......... A61B 6/00; A61B 6/04; A61B 6/0492; A61B 6/10; A61B 6/107; A61B 6/14; A61B 6/145; A61B 6/5294; A61B 6/582; A61B 6/583; A61B 90/03; A61B 90/04; A61B 2090/033; A61B 2090/0409; A61B 2090/0487; A61N 5/10; A61N 5/103; A61N 5/1039; A61N 5/1048; A61N 5/1049; A61N 5/1075; A61N 2005/1076; A61N 2005/1094
See application file for complete search history.

(56) References Cited

U.S. PATENT DOCUMENTS

| | | |
|---|---|---|
| 4,223,229 A | 9/1980 | Perisco et al. |
| 2011/0240036 A1 | 10/2011 | Westbrook et al. |

(Continued)

OTHER PUBLICATIONS

Wilke C.T., Zaid, M., Chung, C. et al., "Design and fabrication of a 3D—printed oral stent for head and neck radiotherapy from routine diagnostic imaging," 3D Print Medicine, Springer International Publishing, pp. 1-6, 3:12, Nov. 16, 2017 (https://doi.org/10.1186/s41205-017-0021-4).

(Continued)

*Primary Examiner* — Anastasia Midkiff
(74) *Attorney, Agent, or Firm* — Neal Marcus

(57) ABSTRACT

A method is disclosed of making a customized intraoral positioning device to be positioned within a patient's mouth for radiation therapy planning and treatment of a head and/or neck of the patient.

21 Claims, 11 Drawing Sheets

Related U.S. Application Data

(60) Provisional application No. 62/399,491, filed on Sep. 26, 2016, provisional application No. 62/399,490, filed on Sep. 26, 2016.

(51) Int. Cl.
  *A61B 90/10* (2016.01)
  *A61B 90/14* (2016.01)
  *A61B 90/16* (2016.01)

(52) U.S. Cl.
  CPC ............. *A61N 2005/1076* (2013.01); *A61N 2005/1094* (2013.01)

(56) References Cited

U.S. PATENT DOCUMENTS

| | | |
|---|---|---|
| 2011/0291031 A1 | 12/2011 | Johnson et al. |
| 2012/0012120 A1* | 1/2012 | Giffey ................. A61B 1/24 |
| | | 128/860 |
| 2012/0167897 A1 | 7/2012 | Bettega |
| 2013/0131427 A1 | 5/2013 | Johnson et al. |
| 2014/0109919 A1 | 4/2014 | Crout |
| 2015/0041685 A1 | 2/2015 | Koller et al. |
| 2016/0135925 A1 | 5/2016 | Mason et al. |

OTHER PUBLICATIONS

International Search Report and Written Opinion dated Dec. 5, 2017 for PCT/US17/52821.
International Search Report and Written Opinion dated Dec. 5, 2017 for PCT/US17/52825.

* cited by examiner

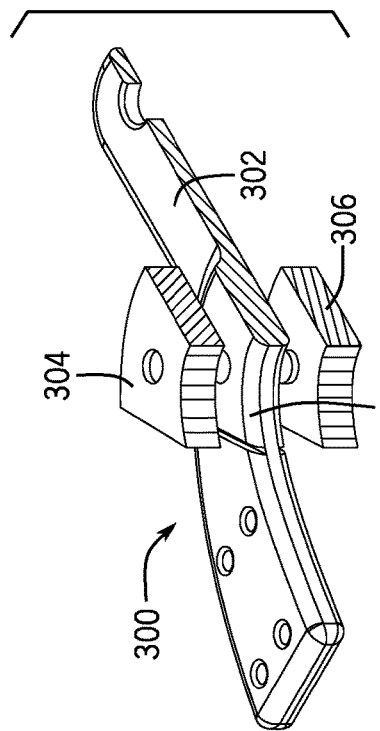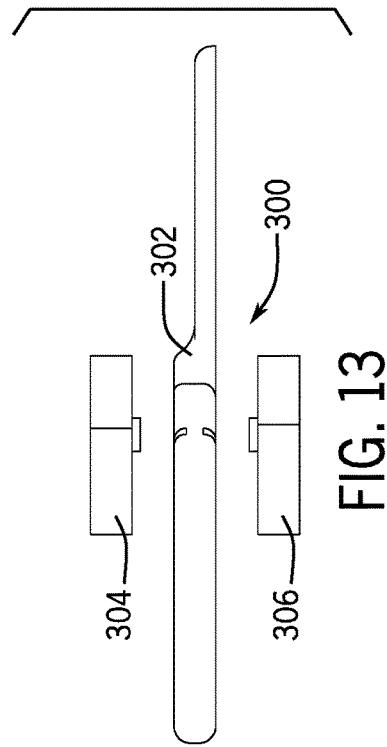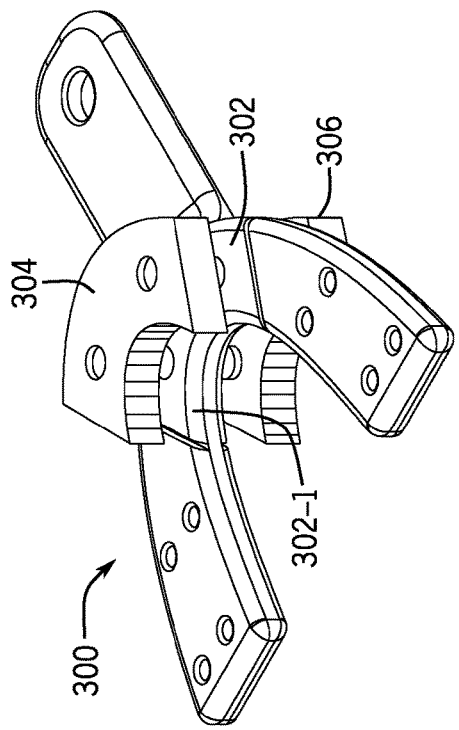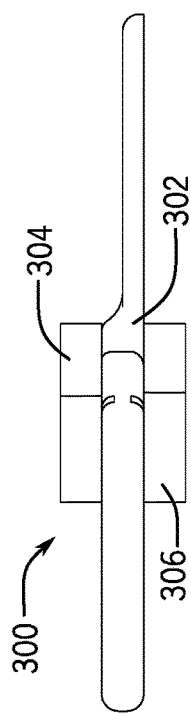
FIG. 11
FIG. 13
FIG. 10
FIG. 12

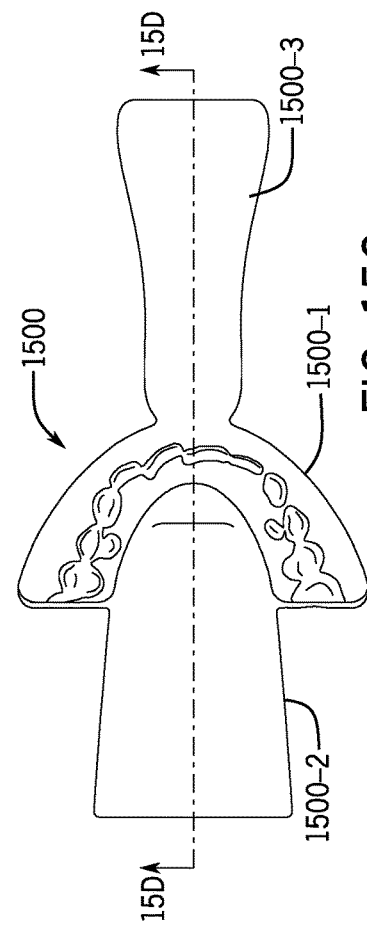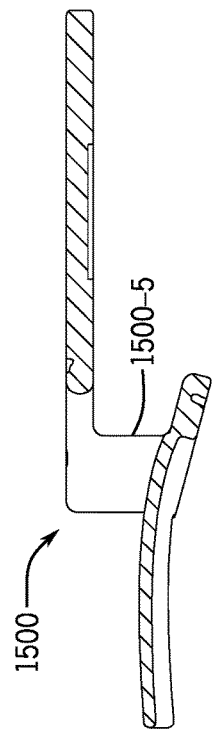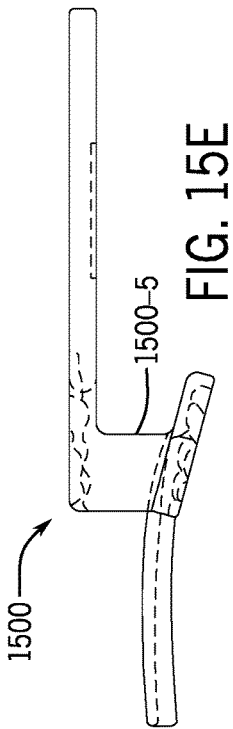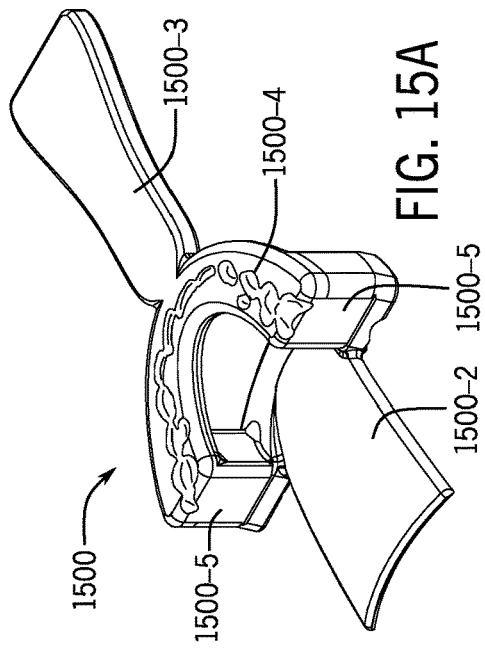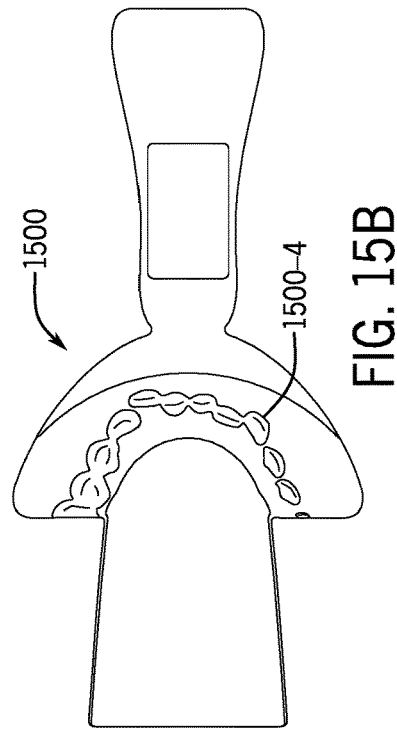

METHOD OF MAKING A CUSTOMIZED INTRAORAL POSITIONING DEVICE FOR USER RADIATION THERAPY TREATMENT

REFERENCE TO RELATED APPLICATIONS

This application is a continuation application of International Application Number PCT/US16/52821, filed on Sep. 21, 2017 entitled "Method of Making a Customized Intraoral Positioning Device For User Radiation Therapy Treatment" which claims priority to U.S. provisional application No. 62/399,491, filed Sep. 26, 2016 entitled "Intraoral Positioning Device" and U.S. provisional application No. 62/399,490, filed on Sep. 26, 2016 entitled "Method of Making Intraoral Positioning Devices for User Radiation Therapy Treatment and Registration Device for Method" which are all incorporated by reference herein.

FIELD OF THE INVENTION

The present invention relates to a method of making a customized intraoral positioning device for user radiation therapy treatment.

BACKGROUND OF THE INVENTION

Over the last 10 years, head and neck cancer diagnoses have increased annually by ten to fifteen percent. The rise in occurrence is largely the result of the increase in HPV infections. Radiation therapy (e.g. Intensity modulated radiation therapy treatment, IMRT, or intensity modulated proton therapy, IMPT) is a primary treatment modality along with surgery, and chemotherapy for such cancers. In IMRT and IMPT, patient target locations are treated with small beams of high intensity radiation that are delivered from multiple directions to conform to the shape of the tumor while avoiding healthy anatomic structures to reduce radiation exposure. In order for radiation therapy to be effective, i.e., to reduce or remove malignant tumors, the patient must remain in position and motionless during many repeatable treatment sessions (e.g. 30). Prior devices for IMRT treatments, however, have been less than effective for such purposes when it comes to positioning the dental structures (e.g., lower jaw) including the tongue. This is due to the inadequacy of prior methods and products used to make such devices.

SUMMARY OF THE INVENTION

Embodiments of a method of making a customized intraoral positioning device for user radiation therapy treatment are disclosed.

In accordance with an embodiment of this disclosure, a method is disclosed of making a customized intraoral positioning device to be positioned within a patient's mouth for radiation therapy planning and treatment for a head and/or neck of the patient, the method comprising: receiving a prescribed treatment plan using and the intraoral positioning device, wherein the prescribed treatment plan includes an incisor separation and/or tongue position of the patient; introducing a registration device into the patient's mouth to a position to align the upper and lower arches at the incisor separation; digitizing the upper and lower arches with the registration device in alignment so as to obtain a relationship between the upper and lower arches at the prescribed incisor separation; and creating a customized intraoral positioning device for the patient based on the relationship between the upper and lower arches at the incisor separation and prescribed treatment plan.

In accordance with another embodiment of this disclosure, a method is disclosed of making a customized intraoral positioning device to be positioned within a patient's mouth for radiation therapy planning and treatment of a head and/or neck of the patient, the method comprising: receiving a prescribed treatment plan using the customized intraoral positioning device, wherein the treatment plan includes a prescribed incisor separation and/or tongue position of the patient for intended treatment; creating impressions of the patient's upper and lower arches of the patient's mouth; introducing a registration device into the patient's mouth to position the upper and lower arches at the prescribed incisor separation, so as to enable a model of the patient's upper and lower arches to be registered; creating models of the patients upper and lower arches based upon the impressions of the patient's upper and lower arches; digitizing the models of the patient's upper and lower arches; assembling the models of the patient's upper and lower arches on registration device; and digitizing the assembly of the models on the registration device so as to obtain a relationship between the upper and lower arches at the prescribed incisor separation.

In accordance with another embodiment of this disclosure, method of making a customized intraoral positioning device to be positioned within a patient's mouth for a prescribed radiation therapy treatment plan for a head and/or neck of the patient, wherein the prescribed radiation treatment plan includes separation of incisors, the method comprising obtaining dental records using digital scanning or imaging; introducing a registration device into the patient's mouth at a set separation to obtain positioning data including a relationship between upper and lower arches of the patient's mouth; and combining obtained positioning data, dental records the prescribed radiation treatment plan to create a customized intraoral positioning device for the patient.

BRIEF DESCRIPTION OF THE DRAWINGS

FIGS. 10-13 depict various views of exploded and assembled views of the registration device shown in FIGS. 3-9.

FIGS. 15A-15E depict various views of another example intraoral positioning device that is customized for a patient using the method of making the intraoral positioning device shown in FIG. 2.

DETAILED DESCRIPTION OF THE INVENTION

Embodiments of a method of making intraoral positioning devices (IPDs) for user radiation treatment and a registration device for the method are described herein with reference to the drawings. (The registration device may also be referred to as an open bite registration device.)

The embodiment for the method involves the design, configuration and manufacture of the IPDs. The method employs the embodiments of the registration device disclosed below. An IPD is configured to be positioned within a patient's mouth for use during intensity-modulated radiation therapy (IMRT), intensity-modulated proton therapy (IMPT), planning, imaging and treatment. With the method described herein, the IPD is created as a customized device for a particular user (patient). In this respect, the IPD is specifically designed and manufactured to a specific patient (user) based on the patient's anatomic structure and doctor's prescribed treatment plan. FIGS. 1A-1E depict several views of an example customized IPD (IPD 100). In this example, IPD 100 is configured or manufactured as one-piece (integral). (FIGS. 15A-15E depict several views of another example customized IPD 1500). These are only examples of customized IPDs.

In brief, the example (shown in FIGS. 1A-1E) patient customized IPD 100 is fitted within a patient's mouth in a prescribed position to engage the patient's dental structures (e.g., teeth, arches, pallet, and tongue) for user radiation planning and treatment including intensity-modulated radiation therapy (IMRT), intensity-modulated proton therapy (IMPT) and other radiation planning and treatment methods known to those skilled in the art. IPD 100 is a device that reproducibly positions oral structures in a prescribed manor (e.g. positioning that maximizes separation between target and non-target structures thereby sparing such tissue unnecessary exposure to radiation). For description purposes, IPD 100 is broken down into three sections or parts. These sections are bite stent 101-1 (section), tongue displacement stent 101-2 and deployment handle or pull tab 101-3.

Figure 1C:
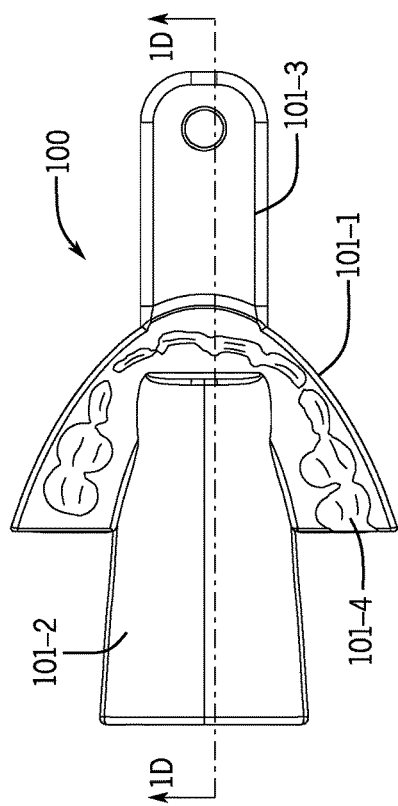
FIGS. 1A-1E depict different views of an example intraoral positioning device that is customized for a patient using the method of making the intraoral positioning device.
Figure 1D:
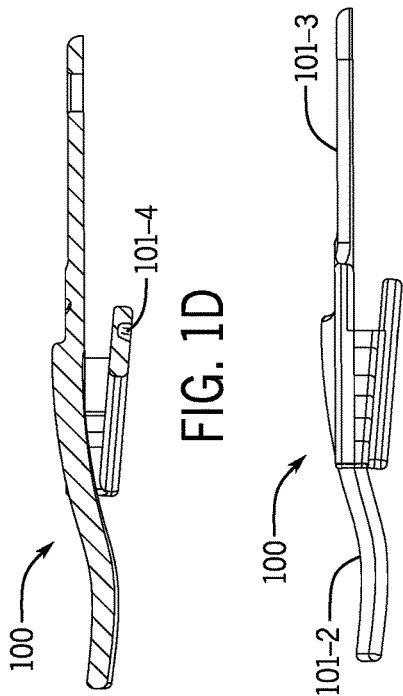
Figure 1E:
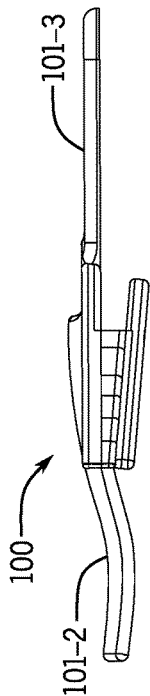
Figure 1A:
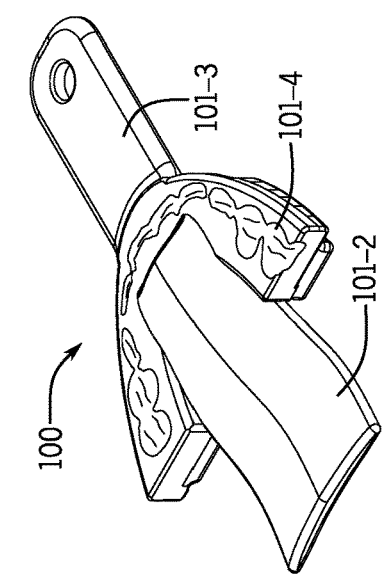
Figure 1B:
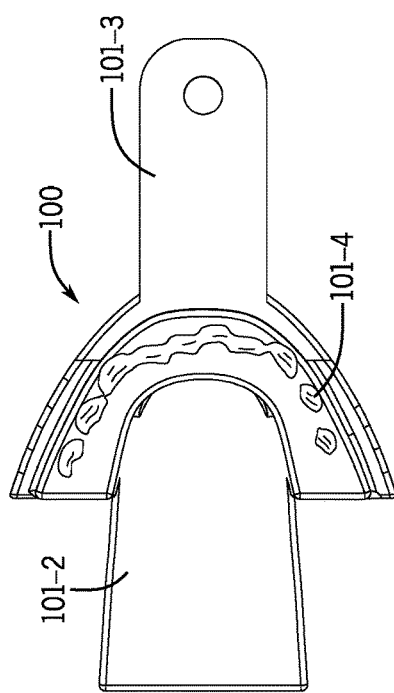

FIG. 1A is a rear perspective view showing a final representation of IPD 100 depicting the top set of teeth impressions 101-4 that allow for precise positioning and a secure fit. Tongue displacement stent 101-2 is a vertical depression stent with slight curve to position the tongue as prescribed. However, it may be configured in any of a number of ways as known by those skilled in the arts (e.g., lateral tongue positioning, vertical lift tongue positioning). FIG. 1B depicts a bottom plan view of IPD 100 illustrating a small size difference between the upper and lower arches which is part of the patient specific design that was adjusted based on the patient's anatomy, i.e., upper and lower jaw size. The lower set of teeth impressions 101-4 is also shown. FIG. 1C depicts a top plan view of IPD 100. FIG. 1D depicts a side cut away view with upper and lower arches. IPD 100 is shown extending to the rear (left) and the pull tab 101-3 extends to the front (right). The separation blocks are seen with gaps between them that allow for air flow, thereby allowing a patient or user to breath with the device in place. Teeth impressions 101-4 are shown where the upper and lower teeth fit. FIG. 1E depicts a side view where the angle of the patient's jaws can be seen in the relationship between the upper and lower arches.

Figure 2:
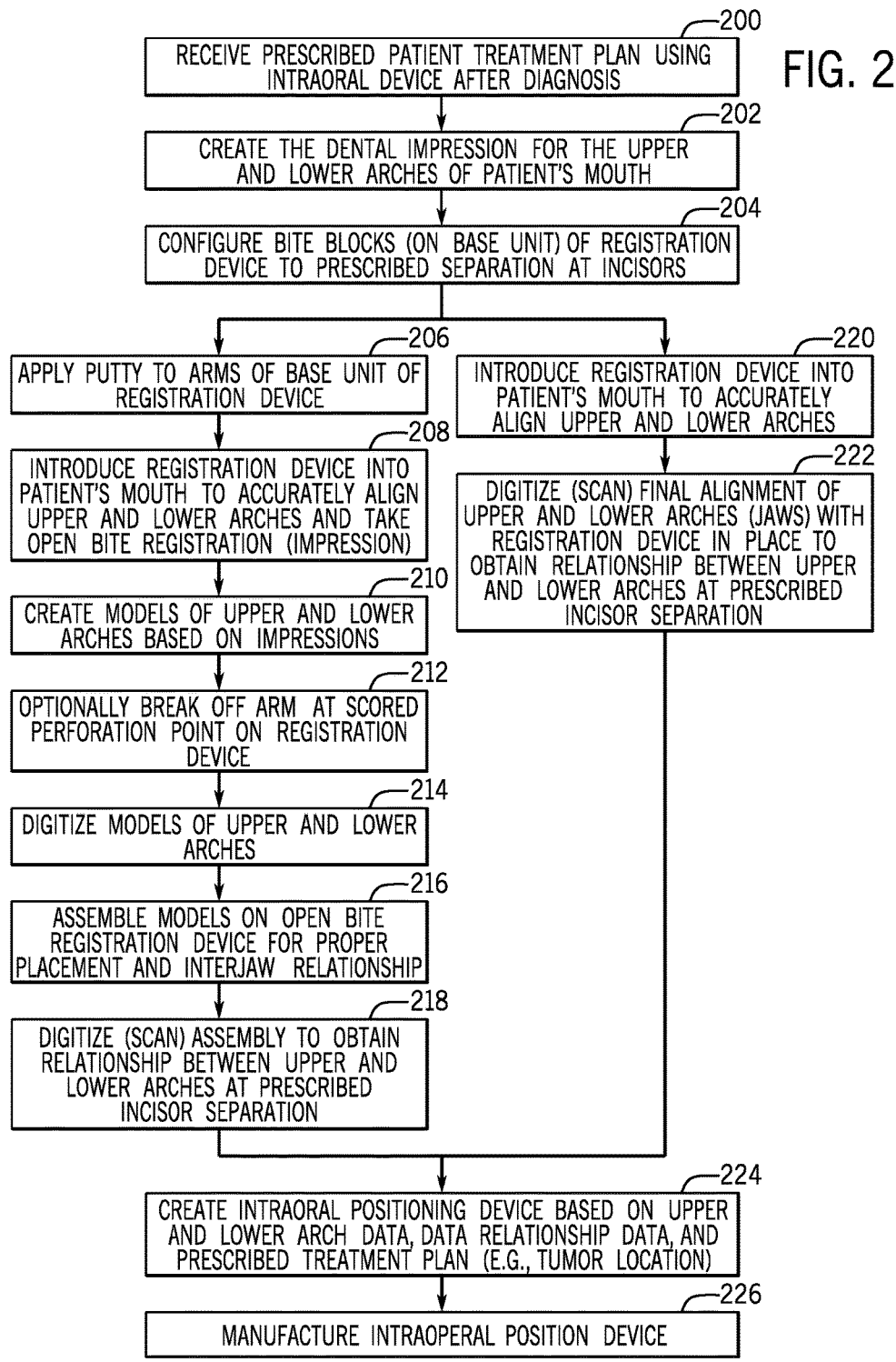
FIG. 2 depicts example steps for the method of making the intraoral positioning device shown in FIGS. 1A-1E.

FIG. 2 depicts a method of making a customizable IPD 100 shown in FIG. 1. Execution begins at step 200 wherein a prescribed patient treatment for using an IPD is received (after diagnosis). In detail, a patient is diagnosed with cancerous tumor or other malady and a doctor will prescribe a treatment plan for the patient. The treatment plan may include surgery and/or radiation therapy. IMRT is one form of treatment as described above. As part of this step, the location of the tumor and area subject to treatment are identified. The doctor will identify the amount of separation desired at the incisors for proper treatment along with the desired position of the tongue and other dental structures (e.g., soft tissue).

Execution proceeds to step 202 wherein upper and lower dental impressions are created. These impressions depict the upper and lower arches, i.e., jaws including the patient's teeth, gums and/or pallet. These impressions may be taken physically by molds (e.g., using impression trays) or digitally (scan) by MRI, CT or other mechanism known to those skilled in the art. In short, dental data records are needed for the method.

At this point, a relationship between the upper and lower jaws at the prescribed incisor separation (also referred to as the interjaw relationship) is needed. In order to accomplish this, the registration device is employed to obtain the interjaw relationship positioning data. This data is then translated into a computer program (e.g., CAD modeling software) along with the patient's dental records. Registration, particularly in the case of an "open bite registration", involves recording accurate positioning data of a patient's dental and oral structures. This includes interjaw relationship data and oral structure data (e.g., teeth, gums, tongue, etc.) The registration device is employed one of two ways to obtain this interjaw relationship data. That is, the dental records, including interjaw relationship may be generated either physically or digitally as known to those skilled in the art (e.g., physical impression molds, interoral scans, computed tomography (CT), Magnetic Resonance Imaging (MRI), etc.). In either case, execution proceeds to step 204 wherein the registration device is initially configured (by a user for a particular patient) by installing bite blocks (304 below) to base unit 302 to increase the height of the arch section to comply with incisor separation as prescribed by a doctor (described in more detail below).

Now, if the interjaw relationship is taken physically (using molds as described above), the method flow follows the path to the left where execution proceeds to step 206 wherein impression putty is applied to the upper and lower arms of the registration device (described in detail below). The putty may be blue moose or another type of substance that forms impressions as known to those skilled in the art.

Execution proceeds to step 208 wherein the registration device (FIGS. 3-13 and described below) is introduced and positioned into the patient's mouth to align upper and lower arches in the prescribed positioning, the impression material is allowed to set or form, and the registration is taken (i.e., an impression).

Execution then proceeds to step 210 wherein models of the patient's upper and lower arches (jaws) are created based on the impressions taken above. An arm (302-2, 302-3 below) of the registration device (as described below) may optionally be cut or broken off (step 212) at a scored perforation point or groove on the base unit 302. The perforation may be configured adjacent an arch section where bite blocks may be installed or at another point as desired during construction. For certain scanning equipment, this will improve scanning accuracy of the position of the maxillary and mandibular jawbones by the software recognition. That is, a scan without the arm will provide accurate data relating to the angle between such jawbones and the fore, aft and lateral position between such jawbones and teeth (with the removable arm in place necessary reference points are often obscured).

Execution then proceeds to steps 214 wherein the models of the patient's upper and lower arches are digitized (scanned) to obtain dental record data such as placement, size and shape of teeth, gingiva, and other structures (or lack thereof).

Execution then proceeds to steps 216 and 218 wherein the models of the patient's arches (e.g., teeth etc.) are assembled on the registration device for proper placement, and the assembly is then digitized (scanned) to obtain the relationship between the upper and lower arches (dental structures) of the patient at the prescribed incisor separation and positioning.

However, for the fully digital version of this process (where steps 206-218 are avoided) execution proceeds to steps 220 and 222 wherein the registration device is introduced into the patient's mouth, and the upper and lower dental structures are aligned in the prescribed position and digitized, i.e., a digital representation is generated of the upper and lower dental structures. That is, one or more points are then scanned to obtain the necessary positioning data (e.g., interjaw relationship and positioning of dental structures).

Now, in either case (whether the flow steps are step 218 or step 222), execution now proceeds to step 224 wherein an IPD is digitally created based on the generated data relating to the patient's anatomic structure (e.g., upper and lower arches, interjaw relationship, dental structures, etc.) and the prescribed treatment plan (e.g. location of treatment area, incisor separation, tongue position, etc.). In this respect, a digital rendering of the IPD is built or developed to fit within the framework of the dental structures (e.g., the upper and lower jawbones).

Then, once complete, the IPD device 100 is manufactured at step 226 using a 3D printer or other manufacturing device known to those skilled in the art.

Figure 4:
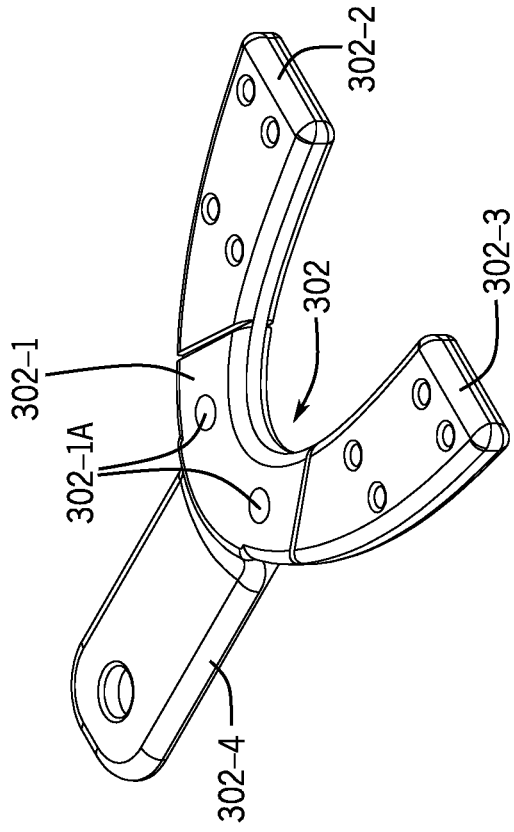
FIGS. 3-5 depict various views of a base unit (component) of an example registration device used in the method of making the intraoral positioning device shown in FIGS. 1A-1E.
Figure 5:
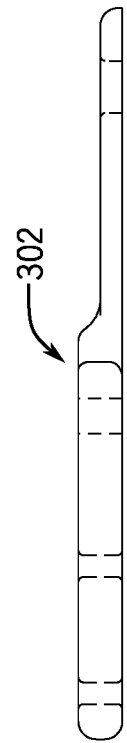
Figure 3:
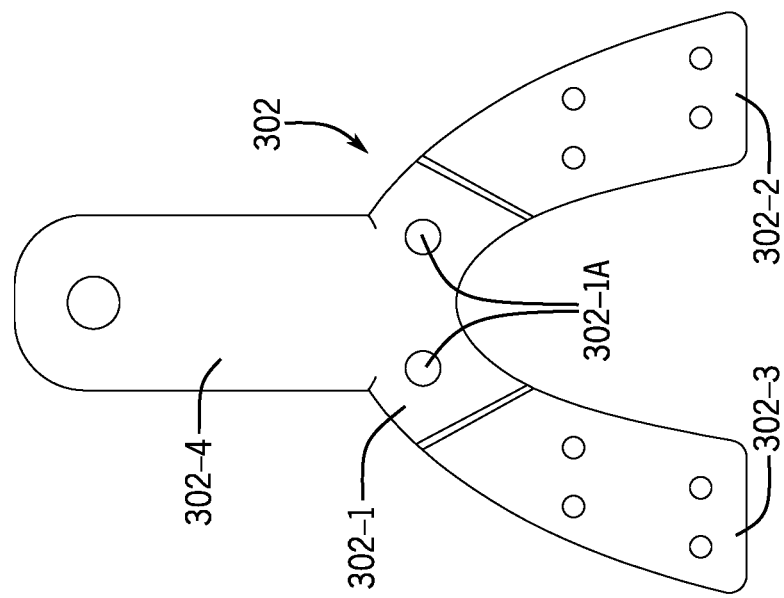
Figure 6:
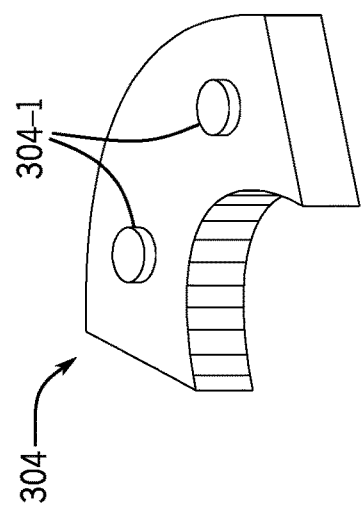
FIGS. 6-9 depict various views of a bite block (component) of an example registration device used in the method of making the intraoral positioning device shown in FIGS. 1A-1E.
Figure 7:
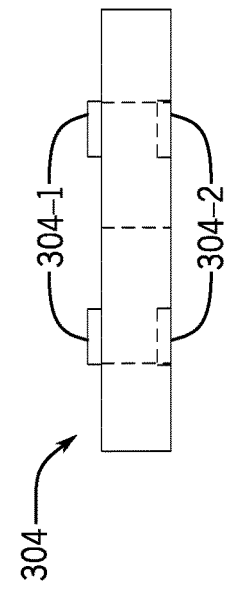
Figure 8:
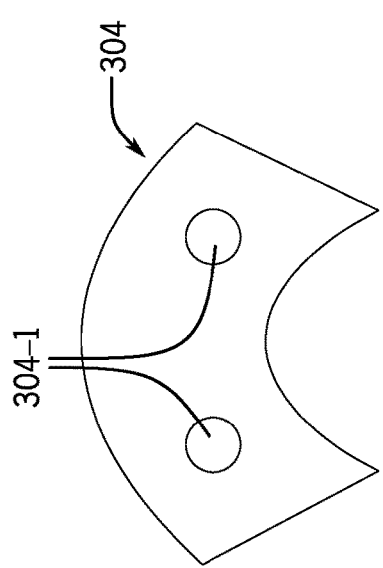
Figure 9:
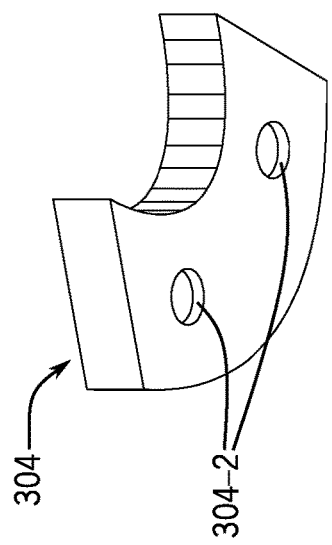

FIGS. 3-13 depict various views of example registration device 300 (and components therefor) used in the method of making the IPD shown in FIGS. 1A-1E (and FIGS. 15A-15E). Device 300 is an open bite registration device. In particular, registration device 300 comprises an arch or base unit 302 and bite blocks 304, 306 that are installed into base unit 302 to increase the height of an arch section 302-1 (below) to comply with incisor separation as prescribed by a doctor (or dentist). As best shown in FIGS. 3-5, base unit 302 is configured in an arch shape that models a standard arch shape of a human jaw. Base unit 302 is constructed in a flat or planar configuration. Base unit 302 has one or more holes 302-1A (recessed parts) within arch section 302-1 to receive projections on bite blocks 304, 306 as described below. In addition, base unit 302 includes two arms 302-2, 302-3, each of which has a plurality of small holes that extend through the arms to receive and ensure that the putty does not move when a patient (user) bites on arms 302-2, 302-3. Bite arms 302-2 and 302-3 may be broken off at the scored perforation points as described in detail below. Base unit 302 further includes a handle 302-4 for grasping and introducing and removing registration device 302 from a patient's mouth.

As seen in FIGS. 6-9, bite blocks are configured or constructed in various sizes to enable a medical professional to build arch section 302-1 to various heights to comply with several incisor separation widths (e.g., 10 or 15 mm separation). Each block includes one or more projections 304-1 (on 304 for example) that extend from one surface thereof that is sized to fit within one or more corresponding holes 302-1A in arch section 302-1 of base unit 302. The projections are configured in a circular shape but those skilled in the art know that they may be rectangular or any other shape (to fit within corresponding openings or holes in arch portion of base unit 302. In design, the projections are sized slightly larger than the openings or holes in the arch section of base unit 302 to ensure that bite blocks do not dislodge from base unit 302 when introduced and placed (and bitten). Bite blocks 304, 306 also include one or more openings or recessed holes 304-2 that may receive projections from another bite block. Alternatively, the projections may each have an annular ring extending outwardly midway around a projection. The annular ring is configured with a larger diameter to provide greater friction to prevent the block from dislodging. This configuration is described below with respect to another embodiment of the bite block.

Base unit 302 further includes two scored perforations or breakaway points that enable a user to optionally break off one of arms 302-2, 302-3. With certain older scanning equipment, the ability to remove an arm can be beneficial to enable a user to scan more accurately (i.e., to obtain a placement reference to properly calculate position and distance between upper and lower teeth). The breakaway points are channels as shown in FIGS. 3 and 4 as scored perforations.

FIGS. 10-13 depict various views of exploded and assembled views of the example registration device shown in FIGS. 3-9. In particular, FIG. 11 depicts a cross section of registration device 300.

Figure 14:
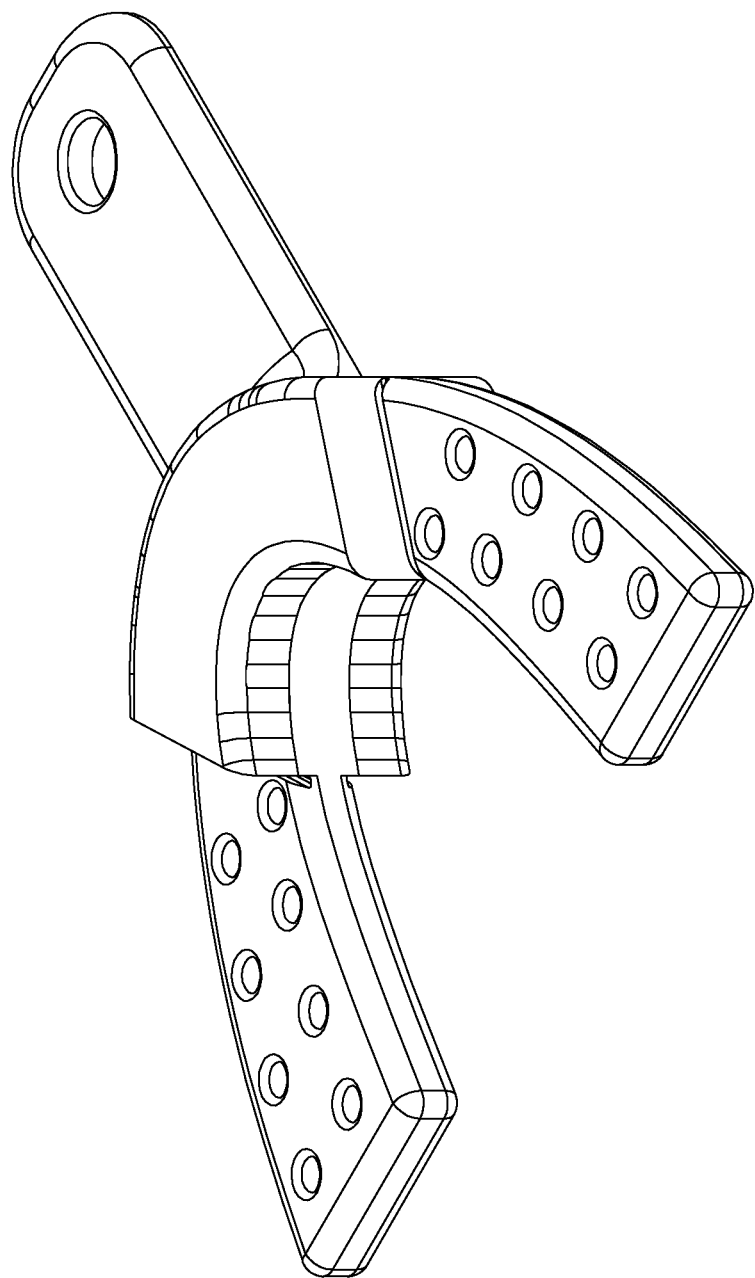
FIG. 14 depicts a view the registration device, in fully deployable configuration with bite blocks and base unit fitted together, used in the method of making the intraoral positioning device shown in FIGS. 1A-1E.

FIG. 14 depicts another example of registration device used in the method of making an IPD. In particular, this view depicts registration device in a fully assembled configuration, with bite blocks installed.

FIGS. 15A-15E depicts different views of an example intraoral positioning device that is customized for a patient using the method of making the intraoral positioning device shown in FIG. 2. In particular, FIG. 15A is a rear perspective view showing a final representation of IPD 1500 depicting the top set of teeth impressions 1501-4 on a bite stent 1500-1 that allow for precise positioning and a secure fit. Tongue displacement stent 1501-2 is a vertical depression stent without a curve to position the tongue as prescribed. FIG. 15B depicts a bottom plan view of IPD 1500 illustrating a small size difference between the upper and lower arches. IPD 1500 is part of the patient specific design that was created based on the patient's anatomy, i.e., upper and lower jaw size and position. The lower set of teeth impressions 1500-4 is also shown. FIG. 15C depicts a top plan view of IPD 1500. FIG. 15D depicts a side cut away view with upper and lower arches. IPD 1500 is shown extending to the rear (left) and the pull tab 1500-3 extends to the front (right). The separation blocks 1500-5 are seen with gaps between them that allow for air flow, thereby allowing a patient or user to breath with the device in place. Teeth impressions 1500-4 are shown where the upper and lower teeth fit. FIG. 15E depicts a side view of IPD 1500.

Figure 17:
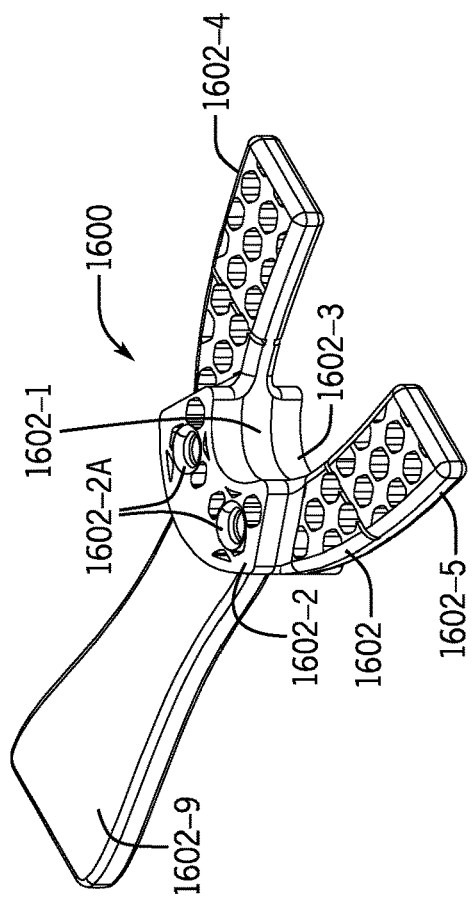
FIGS. 16-18 depict various views of a base unit (component) of an example registration device used in the method of making the intraoral positioning device shown in FIG. 15A-15E.
Figure 18:
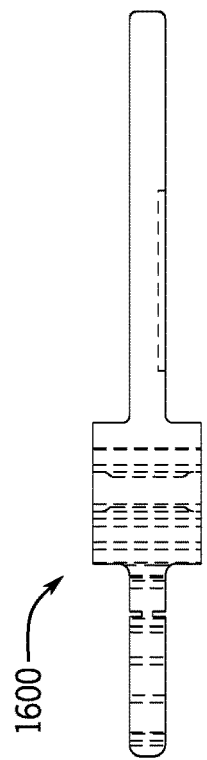
Figure 16:
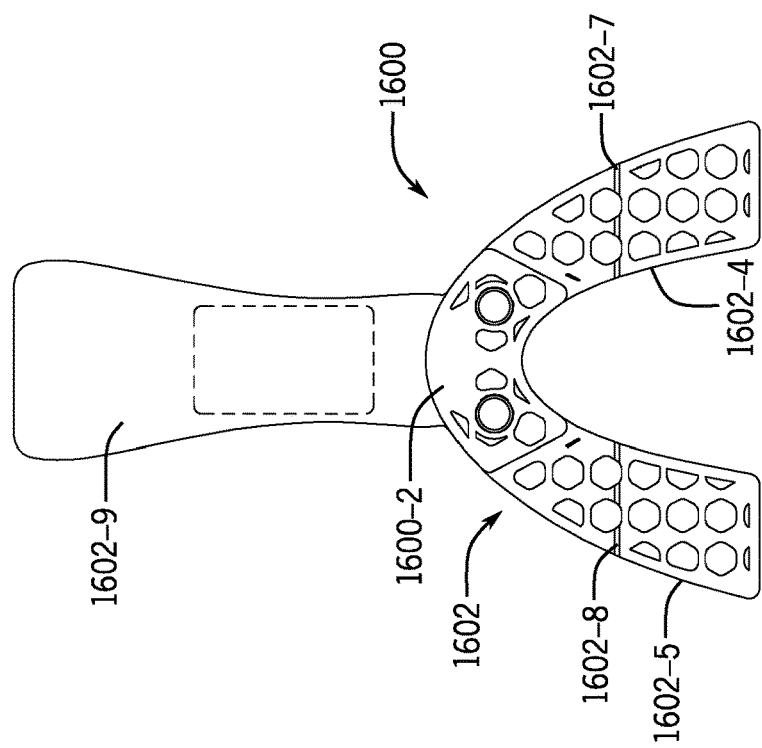
Figure 20:
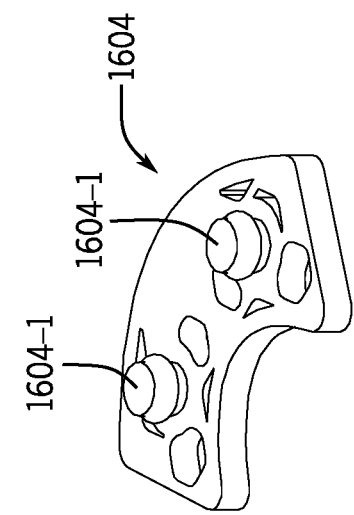
FIGS. 19-22 depict various views of a bite block (component) of the example registration device used with the base unit shown in FIGS. 16-18.
Figure 22:
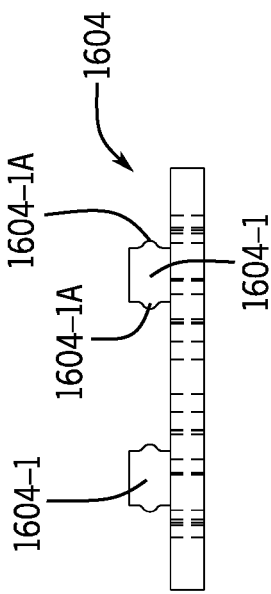

FIGS. 16-27 depict various views of another example registration device 1600 (and components therefor) used in the method of making the IPD described above with respect to FIG. 2. In particular, registration device 1600 comprises an arch or base unit 1602 and bite blocks 1602, 1604 that are installed into base unit 1602 to increase the height of an arch section 1602-1 (below) to comply with incisor separation as prescribed by a doctor (or dentist). As best shown in FIGS. 16-18, base unit 1602 is configured in an arch shape that models a standard arch shape of a human jaw. In this example, base unit 1602 is constructed in a general flat or planar configuration, but in this example, base unit 1602 includes integral bite blocks 1602-2, 1602-3 on opposing sides of arch section 1602-1 (between the arms) respectively as shown. Integral bite block(s) 1602-2 and or 1602-3 are configured to increase the total height of registration device 1600 at the arch 1602-1 to comply with prescribed incisor separation. Bite blocks 1604, 1606 are configured to fit on these integral bite blocks as described below.

Integral bite blocks 1602-2, 1602-3 of base unit 1602, each have one or more holes 1602-2A (recessed parts) therewithin to receive projections on bite blocks 1604, 1606 as described below. (Holes on integral bite block 1602-3 are not shown in the figures). These holes 1602-2A, each have a diameter that is configured smaller than the diameter of the projections and may include a recessed annular ring section to receive a corresponding annular ring on a projection (as described below). The recessed annular ring is best shown in FIG. 17.

Base unit 1602 includes two bite arms 1602-4, 1602-5 extending outwardly in the arch shape as shown and described, each of which has a plurality of small holes that extend through the arms to receive and ensure that the impression material (e.g., putty) has positive engagement with the surface of arms 1602-4, 1602-5. Bite arms 1602-4 and 1602-5 may be broken off at the scored perforation points or groove 1602-7, 1602-8 as described in detail below. Base unit 1602 further includes a handle 1602-9 for grasping and introducing and removing registration device 1600 from a patient's mouth.

Figure 19:
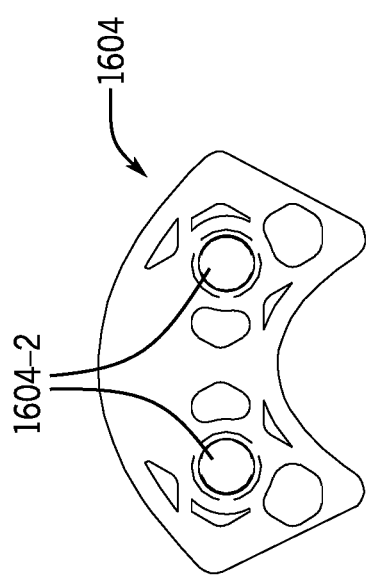
Figure 21:
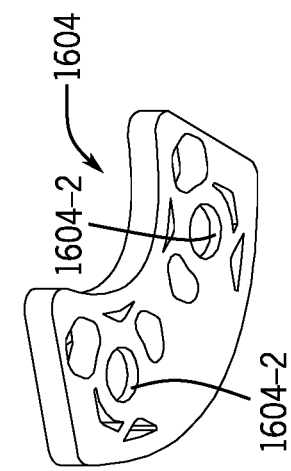
Figure 23:
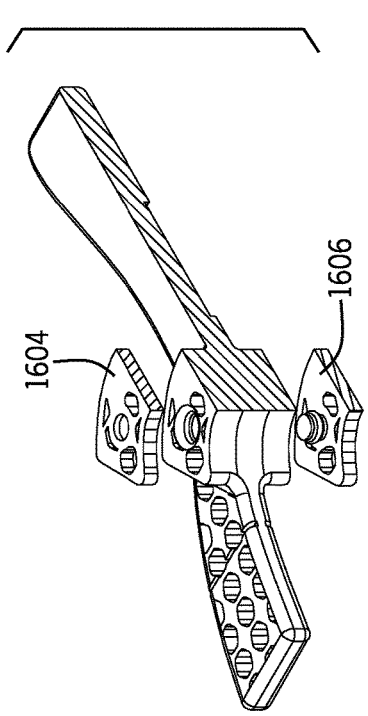
FIGS. 23-26 depict various views of exploded and assembled views of the bite block and base unit of the registration device shown In FIGS. 16-22.
Figure 25:
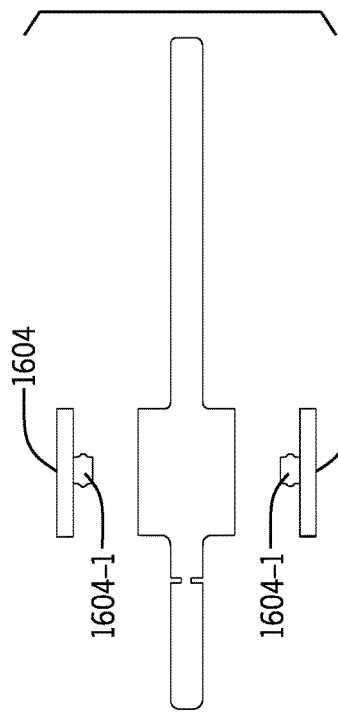
Figure 24:
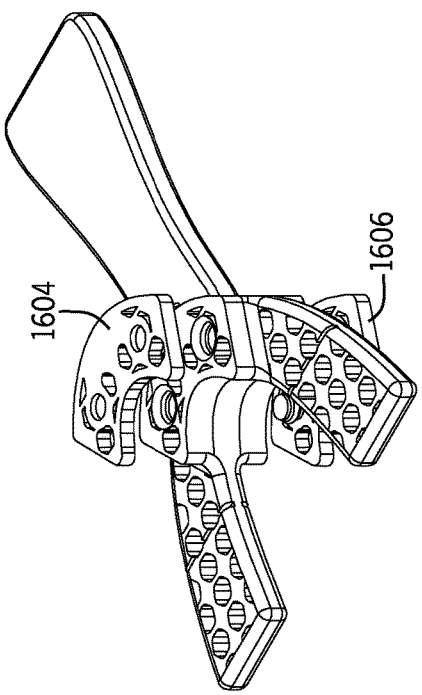
Figure 26:
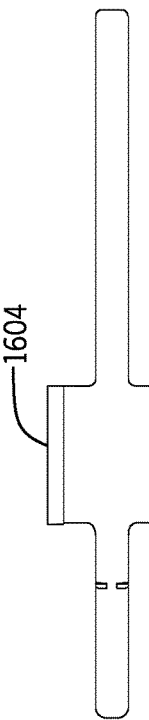

As seen in FIGS. 19-22, bite blocks 1604 are configured or constructed in various sizes (and properly mounted onto the integral bite blocks) that enable a medical professional to securely attach them to registration device 1600, thus creating various heights to comply with multiple incisor separations (e.g., 10 mm or 15 mm . . . ). Each bite block includes one or more projections 1604-1 (on 1604 for example) on one side thereof (surface) as well as holes 1604-2 as shown in FIGS. 19 and 21 (bottom view). Projections 1604-1 are sized to fit securely within corresponding holes 1602-2A in integral bite block in arch section 1602-1 of base unit 1602 (or another bite block). Each bite block also includes holes on the opposing side for received projections of another bite block.

In this example, the projections are configured in a circular shape but those skilled in the art know that they may be rectangular or any other shape (to fit within corresponding openings or holes in arch portion of base unit 1602. Also in this example, these projections each include an annular ring 1604-1A that extends therearound, the diameter of which is sized larger than the corresponding openings or holes 1602-2A in integral bite block 1602-2 (or other bite blocks) to ensure that bite blocks do not dislodge from base unit 1602 when introduced and placed (and bitten). The annular ring 1604-1A may be configured to fit within a corresponding recessed annular ring within corresponding holes in integral bite block to lock the bite block into place. Bite blocks 304, 306 also include one or more openings or recessed holes that may receive projections from another bite block. Alternatively, the projections may each have an annular ring extending outwardly midway around a projection. The annular ring is configured with a larger diameter to provide greater friction to prevent the block from dislodging. Pressure fitments, positive engagement components and other securing methods may be used as known by those skilled in the arts.

In this example, the projections are configured in a circular shape but those skilled in the art know that they may be rectangular or any other shape (to fit within corresponding openings or holes in arch portion of base unit 1602. Also in this example, these projections each include an annular ring 1604-1A that extends therearound, the diameter of which is sized larger than the corresponding openings or holes 1602-2A in integral bite block 1602-2 (or other bite blocks) to ensure that bite blocks do not dislodge from base unit 1602 when introduced and placed (and bitten). The annular ring 1604-1A are may be configured to fit within a corresponding recessed annular ring within corresponding holes in integral bite block to lock the bite block into place. Bite blocks 304, 306 also include one or more openings or recessed holes that may receive projections from another bite block. Alternatively, the projections may each have an annular ring extending outwardly midway around a projection. The annular ring is configured with a larger diameter to provide greater friction to prevent the block from dislodging. Pressure fitments, positive engagement components and other securing methods may be used as known by those skilled in the arts.

Base unit 1602 further includes two scored perforations 1602-7, 1602-8 or breakaway points that enable a user to optionally break off one of arms 1602-2, 1602-3. With certain older scanning equipment, the ability to remove an arm can be beneficial to enable a user to scan more accurately (i.e., to obtain a placement reference to properly calculate position and distance between upper and lower dental structures such as teeth). The breakaway points are channels as best shown in FIGS. 16 and 17 as scored perforations. Note that the perforations 1602-7 and 1602-8 are positioned midway between the arch section and distal end of base unit. These may also be positioned further forward or aft as needed.

Figure 27:
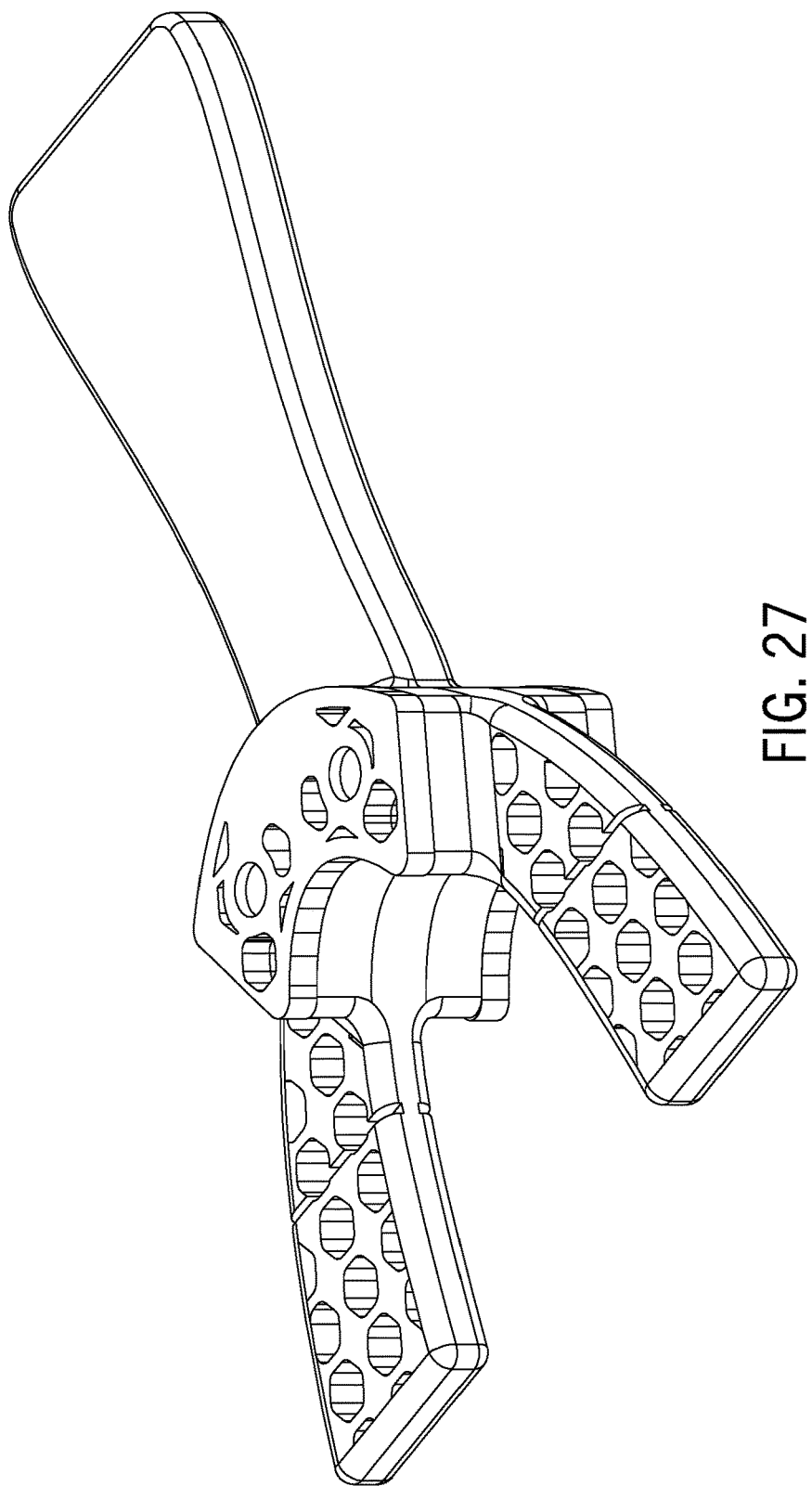
FIG. 27 depicts another view of an enlarged example of the registration device in fully deployable configuration (in a patient's mouth), with bite blocks and base unit fit together, used in the method of making the intraoral positioning device shown in FIG. 15A-15E.

FIGS. 23-26 depict various views of exploded and assembled views of the bite block and base unit of the registration device shown In FIGS. 16-22. FIG. 27 depicts an enlarged view of the example registration device in assembled form.

It is to be understood that the disclosure teaches examples of the illustrative embodiments and that many variations of the invention can easily be devised by those skilled in the art after reading this disclosure and that the scope of the present invention is to be determined by the claims below.

What is claimed is:

1. A method of making a customized intraoral positioning device to be positioned within a patient's mouth for radiation therapy planning and treatment for a head and/or neck of the patient, the method comprising:
    receiving a prescribed treatment plan for using the customized intraoral positioning device, wherein the prescribed treatment plan includes an incisor separation and/or tongue position of the patient;

introducing a registration device into the patient's mouth to a position to align the upper and lower arches at the incisor separation;

generating a digital representation of the upper and lower arches with the registration device in alignment so as to obtain a relationship between the upper and lower arches at the incisor separation; and creating the customized intraoral positioning device for the patient based on the relationship between the upper and lower arches at the incisor separation and prescribed treatment plan.

2. The method of claim 1 further comprising creating dental impressions of upper and lower arches of the patient's mouth, wherein creating dental impressions include taking molds of the upper and lower arches of the patient's mouth.

3. The method of claim 1 further comprising configuring one or more bite blocks on a base of the registration device to a thickness corresponding to the prescribed incisor separation of the patient.

4. The method of claim 3 further comprising applying impression material to one or more arms of the base of the registration device.

5. The method of claim 2 further comprising creating models of the upper and lower arches of the patient's mouth from the dental impressions of the upper and lower arches.

6. The method of claim 5 wherein generating a digital representation includes scanning the models of the upper and lower arches of the patients mouth.

7. The method of claim 5 further comprising assembling the models on the registration device for proper placement at the incisor separation.

8. The method of claim 1 further comprising manufacturing the customized intraoral positioning device.

9. A method of making a customized intraoral positioning device to be positioned within a patient's mouth for a prescribed radiation therapy treatment plan for a head and/or neck of the patient, wherein the prescribed radiation treatment plan includes a separation of incisors of the patient, the method comprising:

obtaining dental records of the patient using digital scanning or imaging;

introducing a registration device into the patient's mouth at the separation of incisors to obtain positioning data including a relationship between upper and lower arches of the patient's mouth; and using the obtained positioning data, the dental records and the prescribed radiation treatment plan to create a customized intraoral positioning device for the patient.

10. The method of claim 9 further comprising creating dental impressions of the upper and lower arches of a patient's mouth, wherein creating dental impressions includes the upper and lower arches, teeth, gums and soft pallet of the patient.

11. The method of claim 9 further comprising configuring one or more bite blocks on a base of the registration device to the prescribed separation of incisors of the patient.

12. The method of claim 11 further comprising taking digital scans of one or more points in the patient's mouth with the registration device deployed.

13. A method of making a customized intraoral positioning device to be positioned within a mouth of a patient for radiation therapy treatment of a head and/or neck of the patient, the method comprising:

(a) receiving digital records of an upper arch and a lower arch of the mouth of the patient;

(b) obtaining a relationship between the upper arch and lower arch at an incisor separation of the patient based on the digital records; and (c) creating the customized intraoral positioning device for the patient based on the relationship between the upper arch and the lower arch at the incisor separation of the patient.

14. The method of 13 further comprising receiving a treatment plan for using the customized intraoral positioning device on the patient, wherein the treatment plan includes the incisor separation and/or a tongue position of the patient.

15. The method of claim 14 further including setting the incisor separation.

16. The method of claim 13 wherein the digital records include computed tomography (CT) and/or magnetic resonance imaging (MRI).

17. A method of making a customized intraoral positioning device to be positioned within a mouth of a patient for radiation therapy treatment of a head and/or neck of the patient, the method comprising:

(a) receiving a prescribed treatment plan for using the customized intraoral positioning device on the patient, wherein the prescribed treatment plan includes an incisor separation;

(b) receiving digital records of an upper arch and lower arch of the mouth of the patient at the incisor separation;

(c) obtaining a relationship between the upper arch and lower arch at the incisor separation based on the digital records; and (d) creating the customized intraoral positioning device for the patient based on the relationship between the upper arch and the lower arch at the incisor separation.

18. The method of claim 17 further including setting the incisor separation.

19. The method of claim 17 wherein the customized intraoral positioning device is created based on the relationship between the upper arch and the lower arch at the incisor separation.

20. The method of claim 17 wherein the digital records include computed tomography (CT) and/or magnetic resonance imaging (MRI).

21. The method of claim 17 wherein the customized intraoral positioning device is created using 3D print manufacturing.

* * * * *